United States Patent [19]

Sims

[11] Patent Number: 5,500,698
[45] Date of Patent: Mar. 19, 1996

[54] OPTICAL INSTRUMENTS SUCH AS RETINOSCOPES WHICH MAY INCORPORATE MULTIPLE LENS ASSEMBLIES AND METHODS OF CALIBRATING SUCH INSTRUMENTS

[76] Inventor: Clinton N. Sims, 3432 West Riverside Dr., Ft. Myers, Fla. 33901

[21] Appl. No.: 184,828

[22] Filed: Jan. 21, 1994

Related U.S. Application Data

[63] Continuation-in-part of Ser. No. 101,402, Aug. 3, 1993, Pat. No. 5,430,508, which is a continuation-in-part of Ser. No. 893,245, Jun. 3, 1992, Pat. No. 5,285,224, which is a continuation-in-part of Ser. No. 526,395, May 21, 1990, Pat. No. 5,120,124, which is a continuation-in-part of Ser. No. 427,724, Oct. 27, 1989, Pat. No. 5,104,214, which is a continuation-in-part of Ser. No. 310,334, Feb. 13, 1989, Pat. No. 4,943,162, which is a continuation-in-part of Ser. No. 116,322, Nov. 2, 1987, Pat. No. 4,840,479, which is a continuation-in-part of Ser. No. 23,980, Mar. 16, 1987, Pat. No. 4,820,040, which is a continuation-in-part of Ser. No. 670,398, Nov. 9, 1984, abandoned.

[51] Int. Cl.$^6$ ........................................................ A61B 3/10
[52] U.S. Cl. .......................... 351/218; 351/205; 351/216
[58] Field of Search ................................. 351/205, 214, 351/216, 217, 218, 221

[56] References Cited

U.S. PATENT DOCUMENTS

| | | | |
|---|---|---|---|
| 579,132 | 8/1897 | Clark | 351/233 |
| 1,222,017 | 4/1917 | Moseley | 351/229 |

(List continued on next page.)

FOREIGN PATENT DOCUMENTS

| | | |
|---|---|---|
| 598683 | 5/1960 | Canada . |
| 820766 | 9/1959 | United Kingdom . |

OTHER PUBLICATIONS

Videotape No. 5063 of the American Academy of Ophthalmology, entitled "Retinoscopy: Plus Cylinder Technique" (copyright 1986).

J. C. Copeland, "Streak Retinoscopy" (undated).
Stokes, "On a Mode of Measuring the Astigmatism of a Defective Eye" (1983).
Dennett, "The Stokes' Lens for Measuring Astigmatism" (1985).
Jackson, "A Trial Set of Small Lenses in a Modified Trial Frame" (1887).
"Dr. Thomson's 1895 Correspondence Course in Optics with Historical Commentary by Monroe J. Hirsch".
Friedman, "The Jackson Crossed Cylinder, A Critique" (1940).
Crisp, "A New Cross–Cylinder Test for Astigmatic Axis, Without Use of Test Type" (1942).
Egan, "R Resume of Crossed Cylinder Application and Theory".
Littmann, "Fundamental Considerations About Opthalmometry".
Wunsch, "The Crossed Cylinder" (chapter 38 of Clinical Ophthalmology (vol 1), Duane, editor (1978).
Kaufman, "Subjective Refraction: Fogging Use of the Astigmatic Dials" (chapter 39 of Clinical Ophthalmology (vol. 1), Duane, editor (1978).

(List continued on next page.)

*Primary Examiner*—William L. Sikes
*Assistant Examiner*—Hung Xuan Dang
*Attorney, Agent, or Firm*—Dean W. Russell; Kilpatrick & Cody

[57] ABSTRACT

Techniques and retinoscopic apparatus for measuring or determining a patient's optical error are disclosed. The techniques include overrefraction and can be performed from a fixed position, avoiding the practitioner's need to move back and forth relative to the patient's eye. Equipment associated with the apparatus is adapted to record the location of the retinoscope slide (relative to its upper or lower position) during the examination to provide information concerning the optical error present in the patient's eye. Other associated equipment can include discs of spherical lenses and devices for limiting relative movement of components of the retinoscopic apparatus.

5 Claims, 6 Drawing Sheets

U.S. PATENT DOCUMENTS

| | | | |
|---|---|---|---|
| 1,266,224 | 5/1918 | Day | 351/229 |
| 1,337,265 | 4/1920 | Poser | 351/229 |
| 1,550,582 | 8/1925 | Sheard | 351/229 |
| 1,594,196 | 7/1926 | Herold et al. | 351/229 |
| 1,794,571 | 3/1931 | Wrighton et al. | 351/229 |
| 2,080,844 | 5/1937 | Wittig | 351/221 |
| 2,147,448 | 2/1939 | Lee | 351/229 |
| 2,204,014 | 6/1940 | Grout | 351/221 |
| 2,256,491 | 9/1941 | Peck et al. | 351/229 |
| 2,333,738 | 11/1943 | Peck et al. | 351/229 |
| 2,501,438 | 3/1950 | Copeland | 351/211 |
| 2,874,610 | 2/1959 | Wright | 359/830 |
| 2,923,200 | 2/1960 | Wright | 351/235 |
| 2,938,426 | 5/1960 | Armbruster et al. | 351/235 |
| 2,968,213 | 1/1961 | Wright et al. | 351/235 |
| 2,995,065 | 8/1961 | Wright et al. | 351/235 |
| 3,015,988 | 1/1962 | Hemstreet | 359/670 |
| 3,019,699 | 2/1962 | Schenk | 351/218 |
| 3,136,839 | 6/1964 | Safir | 356/126 |
| 3,415,594 | 12/1968 | Aulhorn | 351/237 |
| 3,428,398 | 2/1969 | Gottschalk | 355/52 |
| 3,439,978 | 4/1969 | Moore et al. | 351/221 |
| 3,498,699 | 3/1970 | Wilkinson | 351/235 |
| 3,524,702 | 8/1970 | Bellows et al. | 351/211 |
| 3,572,908 | 3/1971 | Grolman | 351/206 |
| 3,597,051 | 8/1971 | Copeland | 351/221 |
| 3,602,580 | 8/1971 | Samuels | 351/211 |
| 3,664,631 | 5/1972 | Guyton | 351/236 |
| 3,776,619 | 12/1973 | Heine | 351/218 |
| 3,785,723 | 1/1974 | Guyton | 351/241 |
| 3,791,719 | 2/1974 | Kratzer et al. | 351/211 |
| 3,819,256 | 6/1974 | Bellows et al. | 351/211 |
| 3,822,932 | 7/1974 | Humphrey | 351/222 |
| 3,832,066 | 8/1974 | Cornsweet | 356/127 |
| 3,841,760 | 10/1974 | Guyton | 356/124 |
| 3,860,330 | 1/1975 | Persson | 351/235 |
| 3,874,774 | 4/1975 | Humphrey | 351/233 |
| 3,880,502 | 4/1975 | Humphrey | 351/246 |
| 3,883,233 | 5/1975 | Guilino | 351/211 |
| 3,969,020 | 7/1976 | Lynn et al. | 351/237 |
| 4,021,102 | 5/1977 | Iizuka | 351/211 |
| 4,105,302 | 8/1978 | Tate, Jr. | 351/210 |
| 4,179,196 | 12/1979 | Persson et al. | 351/237 |
| 4,180,323 | 12/1979 | Persson et al. | 356/3 |
| 4,185,896 | 1/1980 | Buhler | 351/235 |
| 4,190,332 | 2/1980 | Body et al. | 351/211 |
| 4,215,919 | 8/1980 | Rybicki | 351/235 |
| 4,385,813 | 5/1983 | Klein et al. | 351/217 |
| 4,413,891 | 11/1983 | Rybicki | 351/235 |
| 4,426,140 | 1/1984 | Stephens | 351/204 |
| 4,436,390 | 3/1984 | Aoki | 351/234 |
| 4,496,226 | 1/1985 | Augusto et al. | 351/234 |
| 4,523,822 | 6/1985 | Thurston | 351/234 |
| 4,526,449 | 7/1985 | Newman et al. | 351/205 |
| 4,606,524 | 8/1986 | Wood | 248/346 |
| 5,072,347 | 12/1991 | Brunson | 362/286 X |
| 5,189,449 | 2/1993 | Perkins | 351/205 X |

OTHER PUBLICATIONS

Duke–Elder and Abrams, "Ophthalmic Optics in Refraction" (1970) pp. 438–439.

Alverez, "Development of Variable–Focus Lenses and a New Refractor" (1978).

Michaels, Visual Optics and Refraction (chapter 12) (1980).

Guyton, "Automated Clinical Refraction" (chapter 67 of Clinical Opthalmology (vol. 1)), Duane, editor (1985).

Chapter 67 of "Clinical Ophthalmology," vol. 1, ediated by Duane and Jaeger (1986).

Section 36 of Donders, "Accommodation and Refraction of the Eye" (1860 or 1864).

P. 12263 of "The American Encyclopedia and Dictionary of Ophthalmology," vol. 16, ediated by Wood (1920).

Pp. 7195–7197 of "The American Encyclopedia and Dictionary of Opthalmology," vol. 10, edited by Wood (1917).

P. 438 in vol. 5 of "System of Ophthalmology," entitled *Ophthalmic Optics and Refraction*, by Duek–Elder and Agrams (1970).

An advertisement of Stereo Optical Co., Inc. entitled "New Sensitivity for Routine Amsler Grid Testing.".

A brochure of Stereo Optical Co., Inc. entitled "Polarized Threshold Amsler Grid System".

Pp. 449–465 of "System of Diseases of the Eye," vol. 4, edited by Norris and Oliver (1900).

Chapters V and VIII–XII of Thorington, *Refraction and How to Refract*, P. Blakiston's Son & Co. (1900).

PRIOR ART

OPTICAL INSTRUMENTS SUCH AS RETINOSCOPES WHICH MAY INCORPORATE MULTIPLE LENS ASSEMBLIES AND METHODS OF CALIBRATING SUCH INSTRUMENTS

CROSS-REFERENCE TO RELATED APPLICATIONS

This application is a continuation-in-part of application Ser. No. 08/101,402 (now U.S. Pat. No. 5,430,508), filed Aug. 3, 1993, entitled "Refraction Techniques Using Modified Streak Retinoscope Assembly," which application is a continuation-in-part of application Ser. No. 07/893,245 (now U.S. Pat. No. 5,285,224), filed Jun. 3, 1992, entitled "Methods and Apparatus for Determining Refractive Error," which application is a continuation-in-part of application Ser. No. 07/526,395 (now U.S. Pat. No. 5,120,124), filed May 21, 1990, entitled "Devices for Determining the Crossed Cylinder Powers and Axes for Multiple Lens Sets," which application is a continuation-in-part of application Ser. No. 07/427,724 (now U.S. Pat. No. 5,104,214), filed Oct. 27, 1989, entitled "Trial Frames, Adjustable Spectacles and Associated Lens Systems," which application is a continuation-in-part of application Ser. No. 07/310,334 (now U.S. Pat. No. 4,943,162), filed Feb. 13, 1989, entitled "Astigmatic Self-Refractor and Method of Use," which application is a continuation-in-part of application Ser. No. 07/116,322 (now U.S. Pat. No. 4,840,479), filed Nov. 2, 1987, entitled "Crossed Cylinder Lenses Refractor with Three-lens Variable Crossed Cylinder Assembly and Method of Use," which application is a continuation-in-part of application Ser. No. 07/023,980 (now U.S. Pat. No. 4,820,040), filed Mar. 16, 1987, entitled "Crossed Cylinder Lenses Refractor and Method of Use," which application is a continuation of application Ser. No. 06/670,398, filed Nov. 9, 1984 now abandoned, all of which applications are incorporated herein in their entireties by this reference.

FIELD OF THE INVENTION

The present invention relates to apparatus and methods for measuring or determining optical errors in the eyes of humans (or animals) and more particularly to techniques for doing so using a modified streak retinoscope.

BACKGROUND OF THE INVENTION

U.S. Pat. No. 3,597,051 to Copeland, incorporated herein in its entirety by this reference, illustrates an exemplary streak retinoscope assembly. One such commercial assembly, the "Optec 360" retinoscope 10 of FIG. 1, includes a thumb slide 12 adapted to move relative to the retinoscope shaft. As shown in FIG. 2A, advancing slide 12 to its upper position causes the light rays emanating from the retinoscope to be approximately parallel. FIG. 2B, by contrast, illustrates the convergence of the light rays that occurs when slide 12 is moved to its lower position.

Current refraction techniques use the streak retinoscope for neutralizing optical errors. Such techniques are described in, for example, Videotape No. 5063 of the American Academy of Ophthalmology's Continuing Ophthalmic Video Education series, entitled "Retinoscopy: Plus Cylinder Technique," and require use of a phoropter, trial frames, or additional lenses. According to these techniques, the slide of the retinoscope remains in the upper position throughout the retinoscopic process. Only if greater than one diopter of astigmatic error is present do these techniques suggest "enhancing" the patient's cylinder power by lowering the retinoscope slide. By contrast, "enhancing" the streak to estimate the sphere power does not occur.

After the practitioner neutralizes the patient's error by changing the phoropter or trial frame lenses, the values of those lenses are consulted to determine the patient's ocular correction. These refraction techniques essentially use the phoropter or trial frame lenses to make the light rays emanating from the retinoscope conjugate to the patient's fundus. (Although these rays are generally assumed to be parallel for these techniques, my recent empirical studies suggest that they are not for commercially-available retinoscopes.) Doing so in turn causes the rays backscattered by the patient's fundus to be conjugate to the practitioner's eye, permitting neutralization of optical error at a specified working distance.

According to Videotape No. 5063, prior retinoscopic estimating techniques were complex and thus rarely learned or used by the average practitioner. Such "two-handed" techniques require the practitioner to rotate a collar or sleeve on the retinoscope while simultaneously moving the slide up and down, effectively creating "spiral" movement of the slide and sleeve. To perform these techniques, moreover, the practitioner must move back and forth relative to the patient, thereby alternately approaching and receding from the eye under examination. The patient's optical error is then typically estimated based on the width of the focused streak of light emanating from the retinoscope as seen by the practitioner on the patient's pupil. Following "straddling" and other movements of the streak, the patient's cylindrical error axis can ultimately be estimated by comparing the longitudinal axis of the streak to a scale on the phoropter. Moreover, as discussed on page 21 of Dr. J. C. Copeland's manual for "Steak Retinoscopy" printed by Optec, Inc. (which manual is incorporated herein in its entirety by this reference), these prior estimating techniques were "best . . . perform[ed] . . . on the naked eye" and thus did not involve overrefraction of existing prescription lenses.

SUMMARY OF THE INVENTION

The present invention provides retinoscopic techniques for measuring or determining a patient's optical (sphere and cylinder) error. Unlike prior methods, the present techniques can be performed from a fixed position, avoiding the practitioner's need to move back and forth relative to the patient's eye. They also need not involve straddling and can be performed whether or not the patient is wearing existing prescription glasses.

During the examination, equipment connected to the modified streak retinoscope of the invention senses the position of the slide relative to some nominal location (e.g. its upper or lower position), providing information concerning the optical error present in the patient's eye. This information can be used to calculate the resulting power and cylinder axis of appropriate corrective lenses. By contrast with prior retinoscopic techniques, the present invention uses this positional displacement of the lamp filament from the fixed condensing lens within the retinoscope to permit the rays emanating from the device to be conjugate to the patient's fundus.

Figure 1:
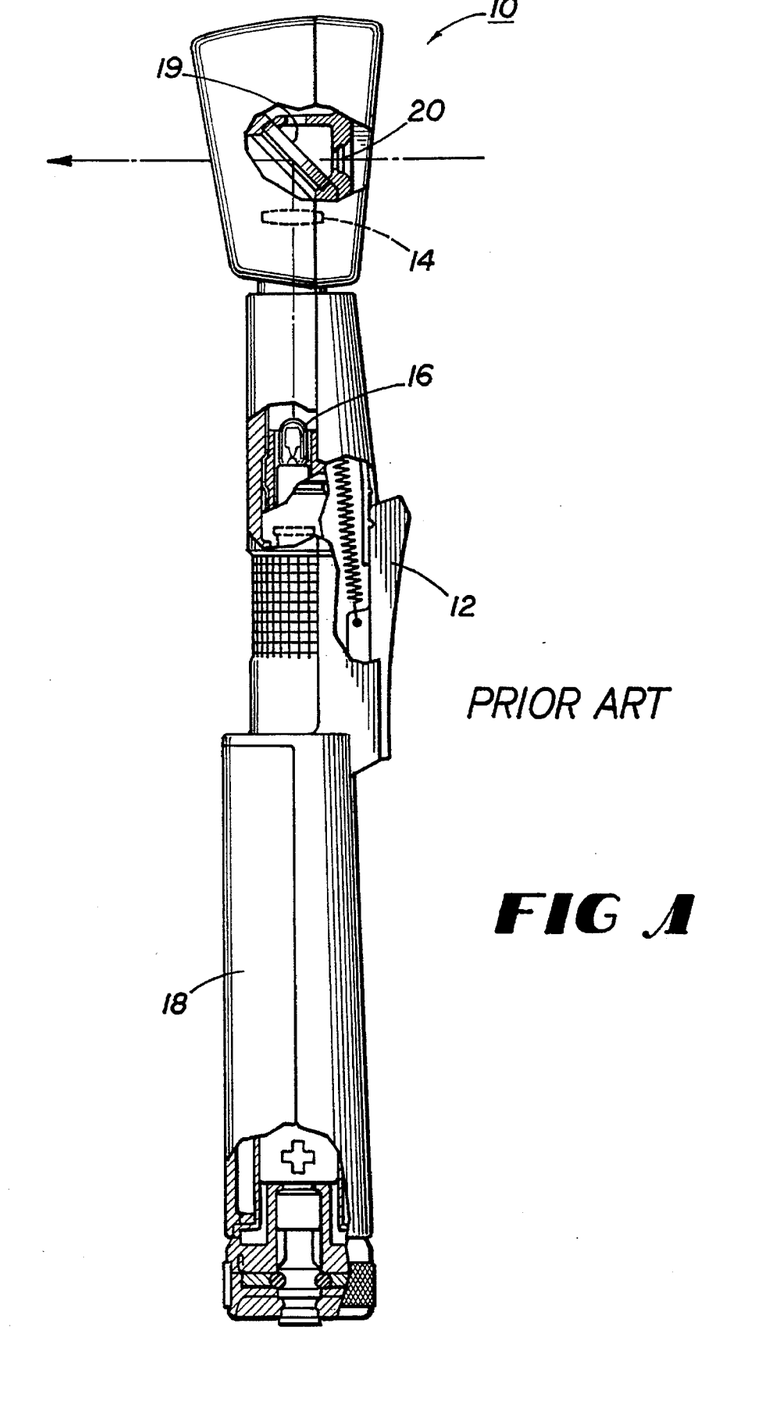
FIG. 1 is an elevational, partially cut-away view of an Optec 360 retinoscope.
Figure 2A:
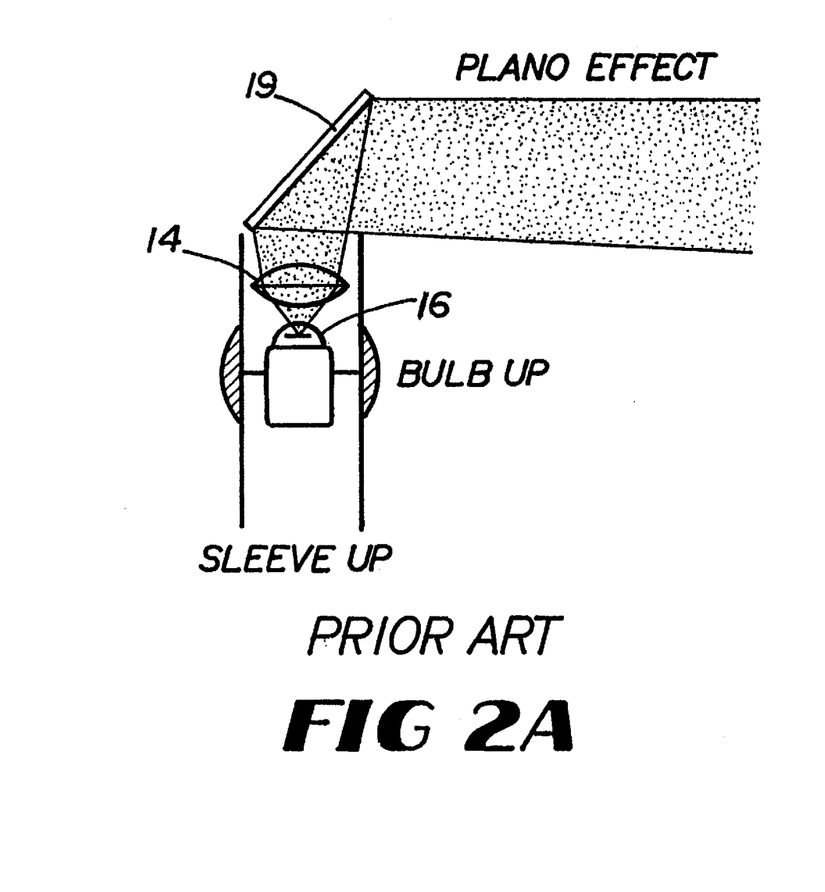
FIG. 2A–B is a schematic representation of the light rays emanating from the Optec 360 retinoscope of FIG. 1 with the slide in its upper position (FIG. 2A) and lower position (FIG. 2B). (Although FIG. 2A–B present the generally-accepted understanding of this representation, my recent empirical studies suggest that the rays emanating from the Optec 360 retinoscope with the slide in its upper position are not parallel but rather slightly divergent.)
Figure 2B:
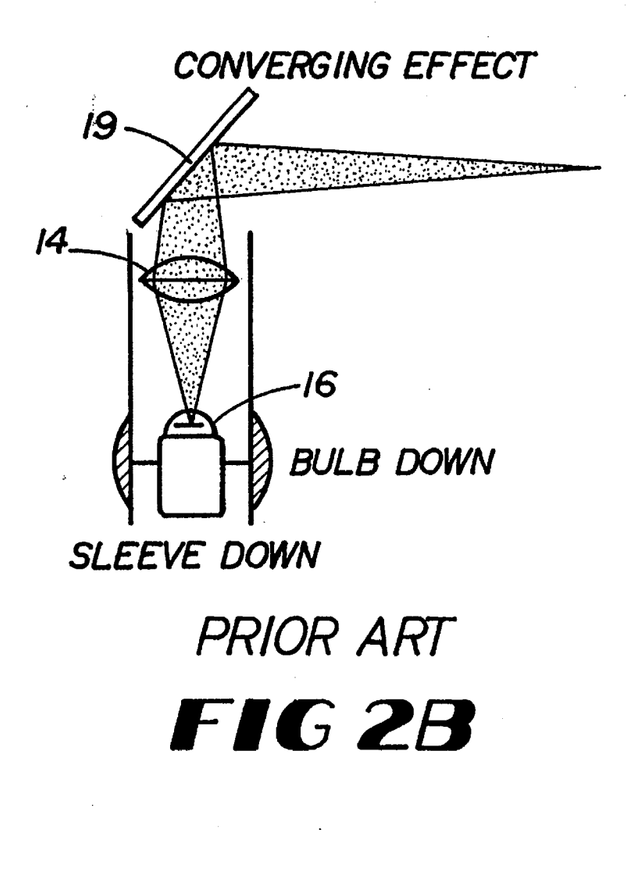

The Optec 360 retinoscope 10 of FIG. 1 contains a +20.00D condensing lens 14 and a bi-pin lamp 16. When slide 12 is in its upper position (FIG. 2A), the filament of lamp 16 is approximately five centimeters from condensing lens 14. The rays emanating from the filament pass through lens 14 as essentially parallel, therefore, thereby focusing those rays at infinity. Displacing slide 12 from its upper position converges the emanating rays relative to condensing lens 14 according to the formula:

$$P=D+(d \times D \times D)-W$$

where P=total vergence power of retinoscopic light rays at the patient's pupil (in diopters)
D=vergence power of emerging retinoscopic light rays (in diopters)
d=distance from the patient's pupil at which retinoscopy is performed (the "working distance") (in meters)
W=working distance (in diopters)
In the slide's lower position on the Optec 360 retinoscope 10 (FIG. 2B), the lamp filament is approximately 6.6 centimeters from condensing lens 14. Accordingly, displacing slide 12 of retinoscope 10 can generate dioptric power ranges as shown below for various (exemplary) working distances:

| Working Distance (centimeters) | Generated Powers (diopters) |
| --- | --- |
| 0.0 | 0.00 to +4.83 |
| 2.54 | −39.40 to −33.98 |
| 10.0 | −10.00 to +2.83 |
| 20.0 | −5.00 to +4.50 |
| 25.0 | −4.00 to +6.67 |
| 33.0 | −3.00 to +9.50 |
| 50.0 | −2.00 to +12.59 |
| 66.0 | −1.50 to +18.80 |
| 100.0 | −1.00 to +26.00 |

By measuring the slide's displacement from, e.g., its upper position, therefore, information concerning the optical power generated using the retinoscope can be obtained at various times during the examination (including when the streak fills the pupil). Embodiments of the modified streak retinoscope of the present invention use a momentary switch and potentiometer connected to the retinoscope to convert this slide displacement quantity into an electrical resistance. This resistance can in turn be measured and used to calculate the optical power necessary to correct the patient's error. The calculation can be performed electronically by a computer adapted to receive the resistance value, for example, permitting the computer to determine the optical correction needed for an over-refracted patient merely by appropriately combining the resistance with the patient's current prescription.

Other embodiments of the apparatus of the present invention can incorporate lens discs or carriers permitting substitution of other power lenses for the +20.00D condensing lens included in the Optec 360 retinoscope 10 of FIG. 1. Alternatively, the powers of these additional lenses can be combined with that of the condensing lens, or the slide displacement can be increased, to enhance the dioptric range of the device. Because the operating principles of some commercial retinoscopes are opposite those of the Optec 360, yet other embodiments of the invention function exactly opposite the manner described above. Further embodiments of the invention include means for limiting the movement of the lamp filament relative to the condensing lens to accommodate, for example, manufacturing variances in existing lamps and lenses.

It is therefore an object of the present invention to provide refraction techniques using a streak retinoscope.

It is another object of the present invention to provide refraction techniques that can be performed by a practitioner from a fixed position relative to a patient.

It is also an object of the present invention to provide overrefraction techniques using a streak retinoscope.

It is a further object of the present invention to provide equipment connected to a streak retinoscope that senses the position of the retinoscope slide relative to some nominal location (e.g. its upper or lower position).

It is yet another object of the present invention to provide a streak retinoscope connected to a momentary switch and potentiometer for converting slide displacement into an electrical resistance.

It is an additional object of the present invention to provide electronic means for converting the sleeve displacement value (and patient's existing prescription if overrefraction is performed) into a resulting optical correction for the patient's eye.

Other objects, features, and advantages of the present invention will become apparent with reference to the remainder of the text and the drawings of this application.

BRIEF DESCRIPTION OF THE DRAWINGS

FIG. 5A–I are selected "streak" images possibly viewed using the modified streak retinoscope of FIG. 3.

FIG. 6A–D are additional streak images possibly viewed using the modified streak retinoscope of FIG. 3.

DETAILED DESCRIPTION

1. Apparatus

As referenced above, FIG. 1 shows an Optec 360 retinoscope 10 having thumb slide 12, condensing lens 14, and lamp 16. Lamp 16 includes a linear filament designed to create the "streak" reflex or reflection seen by the practitioner from the retina of the eye of the patient being examined. Slide 12 moves approximately 1.6 cm along handle 18 so that, in its upper position, the filament of lamp 16 is approximately 5.0 cm from lens 14, which has power of +20.00D. In its lower position, therefore, the filament of lamp 16 is approximately 6.6 cm from lens 14.

In use, light rays emanating from lamp 16 are reflected by mirror 19 approximately 45° into the patient's eye. The practitioner can view the rays backscattered from the patient's retina through a small opening 20 in mirror 19, effectively focusing the backscattered rays into his pupil. In essence, the phoropter or trial frame lenses subsequently placed before the patient are designed to place the patient's eye in focus with the practitioner's eye peering through opening 20.

Figure 3:
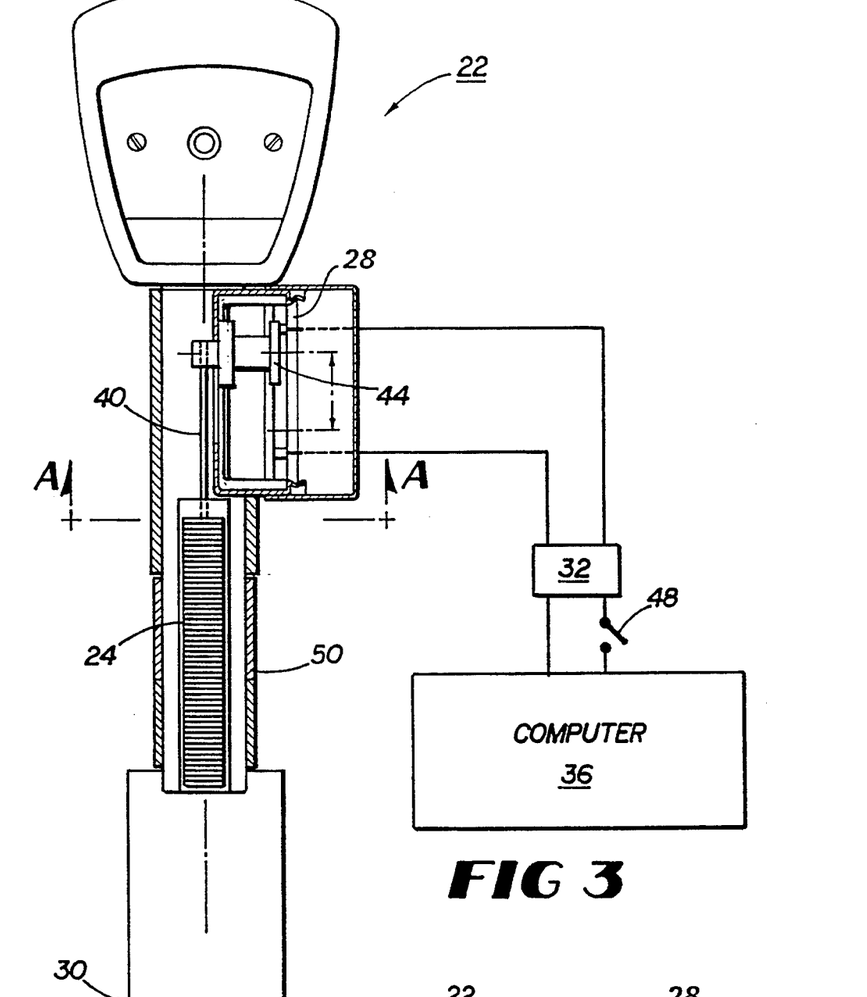
FIG. 3 is an elevational, partially schematicized view of a modified retinoscope of the present invention.
Figure 4:
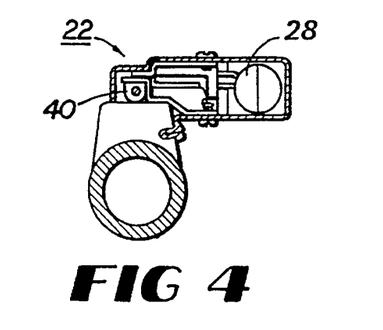
FIG. 4 is a cross-sectional view of the modified retinoscope taken along lines A—A of FIG. 3.

FIGS. 3–4 illustrate a modified streak retinoscope 22 of the present invention. Retinoscope 22 may be a modified Optec 360 retinoscope 10 (FIG. 1) or any other suitable device having a displaceable slide 24 or some other means for moving a lamp relative to a lens. As shown in FIGS. 3–4, retinoscope 22 includes a potentiometer 28 coupled to slide 24, providing means for converting displacement of the slide 24 along handle 30 into an electrical resistance. This resistance can in turn be measured by ohmmeter 32 connected to potentiometer 28 and used by a computer 36 or other appropriate mechanism to calculate the optical power necessary to correct a patient's error. Merely by appropriately combining the resistance measured by ohmmeter 32 with the patient's current prescription using known equations, computer 36 can rapidly and easily determine the optical correction needed for an overrefracted patient.

FIG. 4 details the coupling between potentiometer 28 and slide 24. Wire 40 directly attaches slide 24 to the recording wire or contact arm 44 of potentiometer 28 so that, as slide 24 is displaced (upward or downward) along handle 30, contact arm 44 moves in a corresponding manner. Accordingly, potentiometer 28 tracks movement of slide 24, indicating its deviation from a nominal position. Those skilled in the art will recognize that other means may be used to sense the position of slide 24 along handle 30, including mechanisms electrically or optically coupled to slide 24 or uncoupled but otherwise capable of providing the necessary information. A momentary switch 48 or other suitable device may be included as part of computer 36 (FIG. 3), retinoscope 22, or elsewhere in the circuitry to provide means for indicating the point at which the practitioner determines that a displacement measurement needs to be recorded.

2. Exemplary Operations

To refract a patient's eye using retinoscope 22, the practitioner need merely assume a (fixed) position a known distance (e.g. 50 cm) from the patient.

Figure 5A:
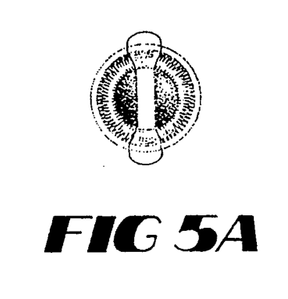
Figures 5B, 5F:
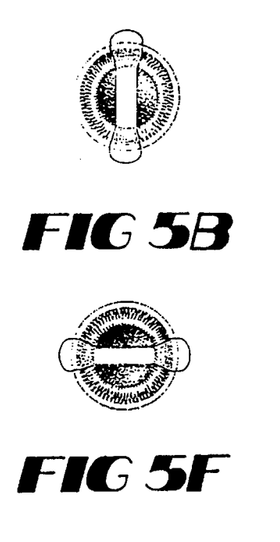
Figures 5C, 5G:
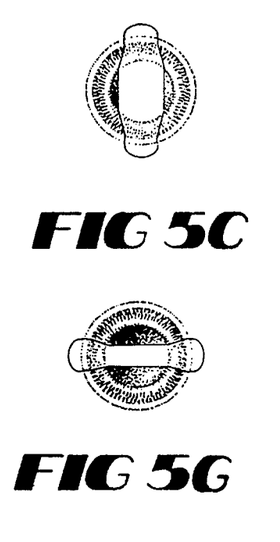
Figures 5D, 5H:
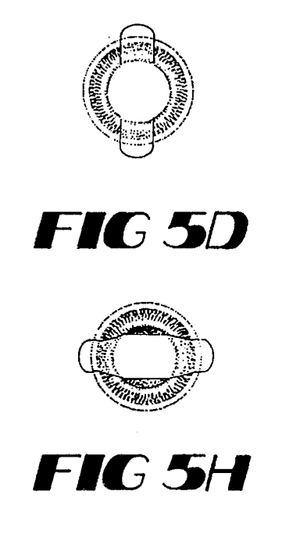
Figures 5E, 5I:
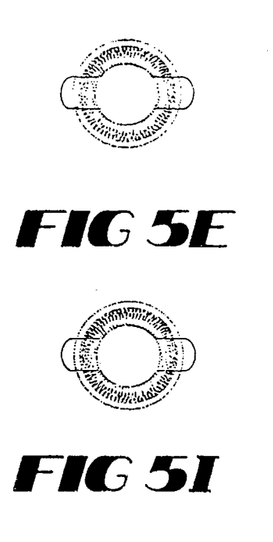
Figure 6A:
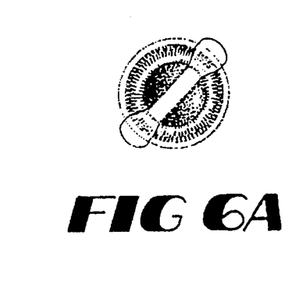
Figure 6B:
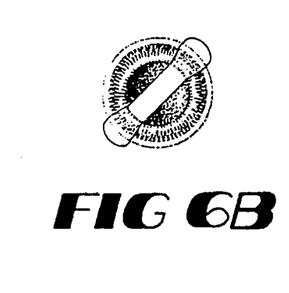
Figure 6C:
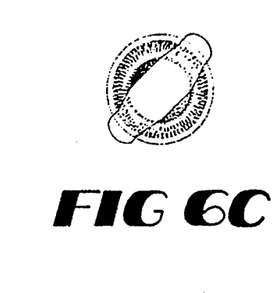
Figure 6D:
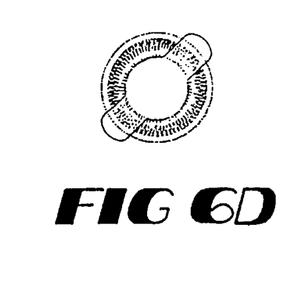

A. For a patient having a solely spherical error between approximately −1.75D and +2.75D, for example, activating retinoscope 22 with slide 24 in its upper position initially provides to the practitioner the streak reflexive image shown in FIG. 5A. Because no astigmatic error is present in this example, neither the width nor intensity of the streak varies as collar or sleeve 50 is rotated ±90°. Lowering slide 24 widens the reflected streak (FIGS. 5B–C) until it fills the patient's pupil as illustrated in FIG. 5D. Again, because the patient has no astigmatic error in this example, rotating sleeve 50 diminishes neither the width nor intensity of the streak (FIG. 5E). At this point momentary switch may be depressed, providing computer 36 information concerning the distance slide 24 has been displaced from its upper position.

B. For a patient having a (solely) spherical refractive error of −2.00D, a retinoscope 22 located 50 cm from the patient's eye, and slide 24 in its upper position, the practitioner will initially view the images of FIGS. 5D–E. Accordingly, no further refractive effort is needed and the initial position of slide 24 is immediately converted into an electrical resistance and transmitted to computer 36.

C. For a patient having a myopic (solely) spherical refractive error greater than −2.00D, the images of FIGS. 5D–E are likely not attainable for working distances of 50 cm or greater. To accommodate these larger spherical errors, the practitioner can place a phoropter or trial frame lens of, for example, between −3.00D and −12.00D before the patient (or use the patient's existing prescription lens) and continue lowering slide 24 until the images of FIGS. 5D–E are obtained. Again, at that point the practitioner can simply activate computer 36 to record the displacement information obtained through potentiometer 28. In this case, however, the power of the phoropter, trial frame, or existing prescription lens must be included in the final corrective calculation (either as a separate input to computer 36 or manually after the displacement information is converted into the refractive error). Alternatively, the practitioner can move toward the patient, decreasing the distance between the retinoscope and eye under examination, until he views the images of FIGS. 5D–E. This decreased working distance must be determined and appropriately factored into the value obtained from computer 36, however.

D. For a patient having a (solely) Spherical error greater than +12.59D, the images of FIGS. 5D–E are similarly not likely to be obtained at a working distance of 50 cm. The practitioner in such a case can place a phoropter or trial frame lens of, for example, between +3.00 and +12.00 before the patient (or again use the patient's existing prescriptive lens). With this lens in place, the practitioner can continue lowering slide 24 until the images of FIGS. 5D–E are obtained, at which point he can activate computer 36 to record the displacement information obtained through potentiometer 28. As in connection with the prior example, the power of the phoropter, trial frame, or existing prescription lens must be included in the final corrective calculation.

E. FIGS. 5F–I and 6A–D illustrate reflections viewed for a patient having a cylindrical error in addition to the spherical errors mentioned in examples A–D. In FIG. 5F–I, the axis of the patient's spherical error is 180°, while in FIG. 6A–D the axis is 45°. For the patient having a cylindrical error principally in the 180° meridian, the practitioner determines the spherical error in the same way as discussed above. Upon rotating sleeve 50 by ±90°, however, the image of FIG. 5F is obtained and the angular orientation of the streak (i.e. 180°) is noted or estimated by the practitioner. The practitioner again lowers slide 24 (FIGS. 5G–H) until the streak fills the pupil (FIG. 5I), at which point computer 36 is utilized to record the displacement of the slide 24. The noted cylinder axis can then be included with the measurements to produce a final corrective prescription.

Embodiments of retinoscope 22 can also incorporate lens discs or carriers to permit lenses of other powers to be substituted for or combined with lens 14. For example, including a disc of spherical lenses in +0.50D increments capable of being optically aligned with opening 20 would enhance the practitioner's ability to use retinoscope 22 accurately at any working distance from 0–100 cm. Incorporating a distance finder into retinoscope 22 would additionally permit electronic measurement of the working distance for input into computer 36, while electrically or otherwise coupling the lens disc to the computer would allow direct input of the added spherical power into the computer 36 for use in later calculations.

Other embodiments of retinoscope 22 function opposite the manner described earlier, recording, for example, the distance slide 24 is displaced from its lower position. These embodiments are designed to accommodate the operating principles utilized in some commercial retinoscopes, in which the light rays from lamp 16 are either focused at infinity (or slightly divergent according to my recent empirical studies) when slide 12 is completed lowered. Yet other embodiments of retinoscope 22 contemplate permitting slide 24 to move more than 1.6 cm, providing a greater range of dioptric powers available for refraction.

Figures 7A, 7B:
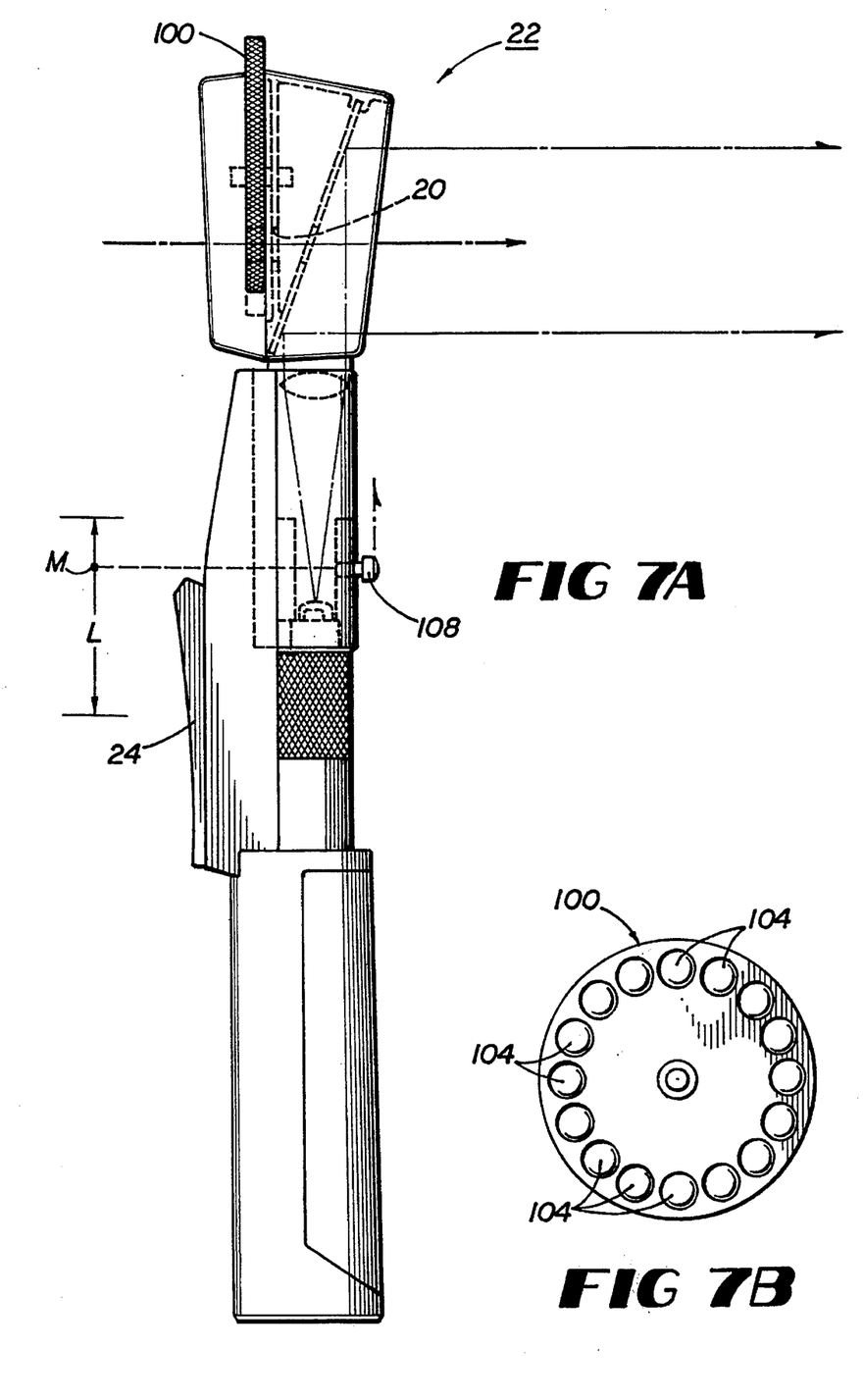
FIG. 7A–B are, respectively, an elevational, partially schematicized view of an alternate retinoscope of the present invention and its associated lens disc.
Figure 8:
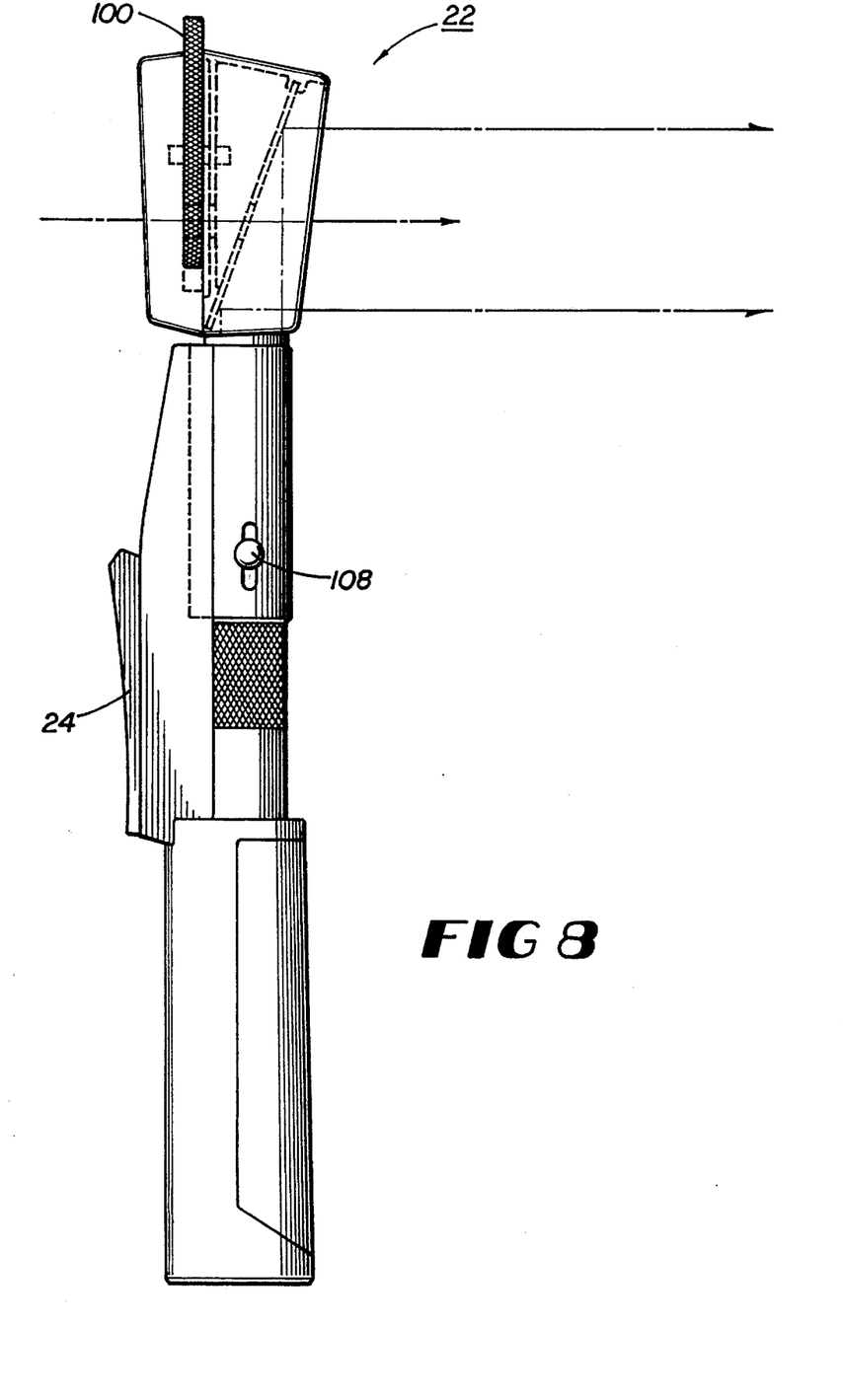
FIG. 8 is another view of the retinoscope of FIG. 7A.

FIGS. 7A–B and 8 illustrate an embodiment of retinoscope 22 adapted as described above to incorporate a disc 100 of spherical lenses 104. Disc 100 is designed to be rotated by the practitioner as needed to align a particular lens 104 with opening 20. Use of disc 100 increases the flexibility of retinoscope 22, permitting, for example, a presbyopic practitioner to view a clearer pupillary image. While maintaining a fixed retinoscopic working distance, disc 100 can also be rotated to provide more or less exact spherical correction. Exemplary lenses 104 for disc 100 may have spherical powers between 0.00 and +5.00D (in 0.25 or 0.50D increments).

Also shown in FIGS. 7A and 8 is knob 108, which may be a set screw or other adjustable device suitable for limiting movement of the filament of lamp 16 relative to lens 14. Empirical evidence suggests that the distance between lens 14 and the filament of lamp 16 when slide 12 is in the upper position differs significantly between versions of existing commercial retinoscopes. Using knob 108 to limit upward travel of the filament of lamp 16 permits retinoscope 22 to be calibrated to neutralize not only this discrepancy, but other manufacturing and assembly variances (including those in lens 14) as well.

Calibration of retinoscope 22 can easily be accomplished by clamping it, for example, 50 cm from a −2.00D (myopic) schematic eye. The position of slide 12 or 24 can then be adjusted until the streak fills the pupil of the schematic eye and knob 108 set to preclude further upward travel of the filament of lamp 16. Similar calibration can occur whenever lamp 16 is replaced. Although the embodiment of retinoscope 22 shown in FIGS. 7A–B and 8 may be coupled directly or indirectly to computer 36, it need not be and is useful manually in improving existing retinoscopic techniques. Manual versions of retinoscope 22 could also be adapted to include an infrared or other distance finder for measuring and displaying the resulting working distance.

The foregoing is provided for purposes of illustrating, explaining, and describing embodiments of the present invention. Modifications and adaptations to these embodiments will be apparent to those of ordinary skill in the art and may be made without departing from the scope or spirit of the invention.

I claim:

1. A method of calibrating a retinoscope comprising the steps of:

a. providing a retinoscope comprising:

i. a handle;

ii. a lamp housed within the handle;

iii. a lens housed within the handle;

iv. a slide displaceable along the handle a maximum distance L to move the lamp within the handle relative to the lens; and v. adjustable means for limiting movement of the lamp within the handle;

b. placing the retinoscope a known distance from a schematic eye having a pupil;

c. displacing the slide along the handle to a point M at which light from the lamp fills the pupil; and d. adjusting the adjustable movement-limiting means to preclude displacement of the slide beyond point M and thereby limit displacement of the slide along the handle to less than the maximum distance L.

2. An optical instrument comprising:

a. a housing having a length;

b. a lens positioned within the housing;

c. a light source positioned within the housing so as to be moveable along its length relative to the lens; and d. means, adjustable when the optical instrument is in use, for limiting movement of the light source along the length of the housing beyond a selected location.

3. An optical instrument according to claim 2 in which the movement-limiting means is a set screw.

4. An optical instrument comprising:

a. a housing having a length and defining a handle;

b. a first lens positioned within the housing;

c. a light source positioned within the housing so as to be moveable along its length relative to the first lens;

d. means, connected to the housing, for optically aligning with the first lens a second lens selected from a group of lenses of varying dioptric power; and e. means, adjustable when the optical instrument is in use, for limiting movement of the light source along the length of the housing beyond a selected location.

5. An optical instrument according to claim 4 in which the optical-aligning means is a disc carrying the group of lenses of varying dioptric power and adapted to rotate relative to the handle.

* * * * *